(12) United States Patent
Campbell et al.

(10) Patent No.: US 7,598,414 B2
(45) Date of Patent: Oct. 6, 2009

(54) METHOD OF MAKING A SYNTHETIC ALKYLARYL SULFONATE

(75) Inventors: Curt B. Campbell, Hercules, CA (US); Gilles Sinquin, Saint Martin du Manoir (FR)

(73) Assignee: Chevron Oronite Company LLC, San Ramon, CA (US)

( * ) Notice: Subject to any disclaimer, the term of this patent is extended or adjusted under 35 U.S.C. 154(b) by 0 days.

(21) Appl. No.: 11/445,794

(22) Filed: Jun. 1, 2006

(65) Prior Publication Data

US 2007/0282125 A1 Dec. 6, 2007

(51) Int. Cl.
C07C 309/00 (2006.01)

(52) U.S. Cl. .......................................... 562/45; 562/91
(58) Field of Classification Search ................... 562/45, 562/91
See application file for complete search history.

(56) References Cited

U.S. PATENT DOCUMENTS

| | | | | |
|---|---|---|---|---|
| 2,469,378 | A | * | 5/1949 | Flett .............................. 562/92 |
| 3,681,442 | A | * | 8/1972 | Bloch et al. .................... 562/94 |
| 3,910,994 | A | * | 10/1975 | Bloch et al. .................... 562/93 |
| 3,953,538 | A | | 4/1976 | Boney |
| 4,085,243 | A | * | 4/1978 | Giordano et al. ............. 427/387 |
| 4,182,613 | A | * | 1/1980 | Stover et al. ................... 44/370 |
| 4,225,737 | A | | 9/1980 | Mikulicz et al. |
| 4,503,277 | A | | 3/1985 | Himes |
| 4,536,301 | A | | 8/1985 | Malloy et al. |
| 4,816,185 | A | | 3/1989 | Parker |
| 5,750,818 | A | | 5/1998 | Mehlberg et al. |
| 6,054,419 | A | | 4/2000 | Le Coent |
| 6,269,881 | B1 | * | 8/2001 | Chou et al. ............... 166/270.1 |
| 6,551,967 | B2 | | 4/2003 | King et al. |
| 6,989,355 | B1 | | 1/2006 | Campbell et al. |
| 7,060,852 | B2 | * | 6/2006 | Maas et al. .................... 562/94 |
| 7,332,460 | B2 | * | 2/2008 | Campbell et al. ........... 507/259 |
| 2004/0010161 | A1 | * | 1/2004 | Maas et al. .................... 562/94 |
| 2004/0030209 | A1 | * | 2/2004 | Narbeshuber et al. ....... 585/323 |
| 2004/0254411 | A1 | * | 12/2004 | Steinbrenner et al. ....... 585/323 |
| 2007/0078075 | A1 | * | 4/2007 | Bottke et al. ................. 510/426 |
| 2007/0142258 | A1 | * | 6/2007 | Steinbrenner et al. ....... 510/202 |

FOREIGN PATENT DOCUMENTS

| | | | |
|---|---|---|---|
| WO | WO 2004058692 A1 | * | 7/2004 |
| WO | WO 2005042448 A1 | * | 5/2005 |
| WO | WO 2005061447 A2 | * | 7/2005 |

* cited by examiner

*Primary Examiner*—Porfirio Nazario Gonzalez
(74) *Attorney, Agent, or Firm*—Josetta I. Jones

(57) ABSTRACT

A process for preparing a synthetic petroleum sulfonate comprising (a) reacting a first amount of at least one aromatic compound with a first amount of a mixture of olefins having from about 8 to about 100 carbon atoms, in the presence of a strong acid catalyst; (b) reacting the product of (a) with an additional amount of at least one aromatic compound and an additional amount of strong acid catalyst and, optionally, with an additional amount of a mixture of olefins selected from olefins having from about 8 to about 100 carbon atoms, in the presence of a strong acid catalyst, wherein the resulting product comprises at least about 80 weight percent of a 1,2,4-trialkylsubstituted aromatic compound; (c) sulfonating the product of (b); and (c) neutralizing the product of (b) with an alkali or alkaline earth metal hydroxide or ammonia.

29 Claims, 1 Drawing Sheet

METHOD OF MAKING A SYNTHETIC ALKYLARYL SULFONATE

BACKGROUND OF THE INVENTION

It is well known to catalyze the alkylation of aromatics with a variety of Lewis or Bronsted acid catalysts. Typical commercial catalysts include phosphoric acid/kieselguhr, aluminum halides, boron trifluoride, antimony chloride, stannic chloride, zinc chloride, onium poly(hydrogen fluoride), and hydrogen fluoride. Alkylation with lower molecular weight olefins, such as propylene, can be carried out in the liquid or vapor phase. For alkylations with higher olefins, such as $C_{16+}$ olefins, the alkylations are done in the liquid phase, often in the presence of hydrogen fluoride. Alkylation of benzene with higher olefins may be difficult, and typically requires hydrogen fluoride treatment. Such a process is disclosed by Himes in U.S. Pat. No. 4,503,277, entitled "HF Regeneration in Aromatic Hydrocarbon Alkylation Process," which is hereby incorporated by reference for all purposes.

1. Field of the Invention

The present invention is directed to a method of making a synthetic alkylaryl sulfonate that is derived by sulfonating an alkylated aromatic compound by reacting an aromatic compound with a mixture of olefins selected from olefins having from about 8 to about 100 carbon atoms in the presence of a strong acid catalyst, whereby the reaction takes place in two reactors in series. The alkylated aromatic compound may be used as an enhanced oil recovery alkylate. These sulfonates exhibit superior performance as enhanced oil recovery surfactants.

2. Description of the Related Art

Mikulicz et al., U.S. Pat. No. 4,225,737, discloses a process for the alkylation of an aromatic hydrocarbon with an olefin-acting alkylating agent. The aromatic hydrocarbon is commingled with a first portion of said alkylating agent in a first alkylation reaction zone at alkylation reaction conditions in contact with a hydrofluoric acid catalyst.

Boney, U.S. Pat. No. 3,953,538 discloses an alkylation process in which a stream of an olefinic material is mixed with an acid stream and polymerized to cause formationi of a polymeric diluent for the high strength acid which is initially charged to the alkylation process.

Mehlberg et al., U.S. Pat. No. 5,750,818 discloses a process for the liquid phase alkylation in an alkylation reactor of a hydrocarbon substrate with an olefinic alkylating agent in the presence of an acid alkylation catalyst at least one hydrocarbon having a lower boiling point than the hydrocarbon substrate and with a substantial stoichiometric excess of the hydrocarbon substrate over the alkylating agent to form a liquid product mixture.

King et al., U.S. Pat. No. 6,551,967 discloses a low over-based alkaline earth metal alkylaryl sulfonate having a Total Base Number of from about 2 to about 30, a dialkylate content of 0% to about 25% and a monoalkylate content of about 75% to about 90% or more, wherein the alkylaryl moiety is alkyltoluene or alkylbenzene in which the alkyl group is a $C_{15}$-$C_{21}$ branched chain alkyl group derived from a propylene oligomer are useful as lubricating oil additives.

LeCoent, U.S. Pat. No. 6,054,419 discloses a mixture of alkyl aryl sulfonates of superalkalinized alkaline earth metals comprising (a) 50 to 85% by weight of a mono alkyl phenyl sulfonate with a C14 to C40 linear chain wherein the molar proportion of phenyl sulfonate substituent in position 1 or position 2 is between 0 and 13% and (b0 15 to 50% by weight of a heavy alkyl aryl sulfonate, wherein the aryl radical is phenyl or not, and the alkyl chains are either two linear alkyl chains with a total number of carbon atoms of 16 to 40, or one or a plurality of branched alkyl chains with on average a total number of carbon atoms of 15 to 48.

Malloy et al., U.S. Pat. No. 4,536,301 discloses a surfactant slug used to recover residual oil in subterranean reservoirs. The slug comprises a mixture of (1) from about 1 to about 10% of a sulfonate of a mixture of mono- and dialkyl-substituted aromatic hydrocarbon which has been obtained by the alkylation of an aromatic hydrocarbon with an olefinic hydrocarbon in the presence of a hydrogen fluoride catalyst; (2) a lower alkyl alcohol which possesses from about 3 to about 6 carbon atoms; and (3) a nonionic cosurfactant comprising an ethoxylated n-alcohol which possesses from about 12 to about 15 carbon atoms.

Campbell et al., U.S. Pat. No. 6,989,355 discloses an under-neutralized alkylxylene sulfonic acid composition for enhanced oil recovery processes. This invention is also directed to a method for enhancing the recovery of oil from a subterranean reservoir which method employs the underneutralized alkylxylene sulfonic acid compositions of the present invention. The under-neutralized alkylxylene sulfonic acid compositions are employed in an aqueous media. The method optionally employs suitable co-surfactants, such as alcohols, alcohol ethers, polyalkylene glycols, poly (oxyalkylene)glycols and/or poly(oxyalkylene)glycol ethers.

Parker, U.S. Pat. No. 4,816,185 discloses reaction products $C_9$-$C_{30}$ alkylbenzenes with styrene and sulfonated derivatives thereof and processes for preparing such products and derivatives. The sulfonate salts of reaction products are especially useful as detergents.

SUMMARY OF THE INVENTION

In its broadest embodiment, the present invention is directed to a process for preparing a synthetic alkylaryl sulfonate comprising (a) reacting a first amount of at least one aromatic compound with a first amount of a mixture of olefins selected from olefins having from about 8 to about 100 carbon atoms, in the presence of a strong acid catalyst; (b) reacting the product of (a) with an additional amount of at least one aromatic compound and an additional amount of strong acid catalyst and, optionally, with an additional amount of a mixture of olefins selected from olefins having from about 8 to about 100 carbon atoms, wherein the resulting product comprises at least about 80 weight percent of a 1, 2, 4 tri-alkylsubstituted aromatic compound; (c) sulfonating the product of (b); and (d) neutralizing the product of (c) with a source of alkali or alkaline earth metal or ammonia.

Accordingly, the present invention relates to a process for preparing a sulfonated alkylated aromatic.

DETAILED DESCRIPTION OF THE INVENTION

Figure 1:
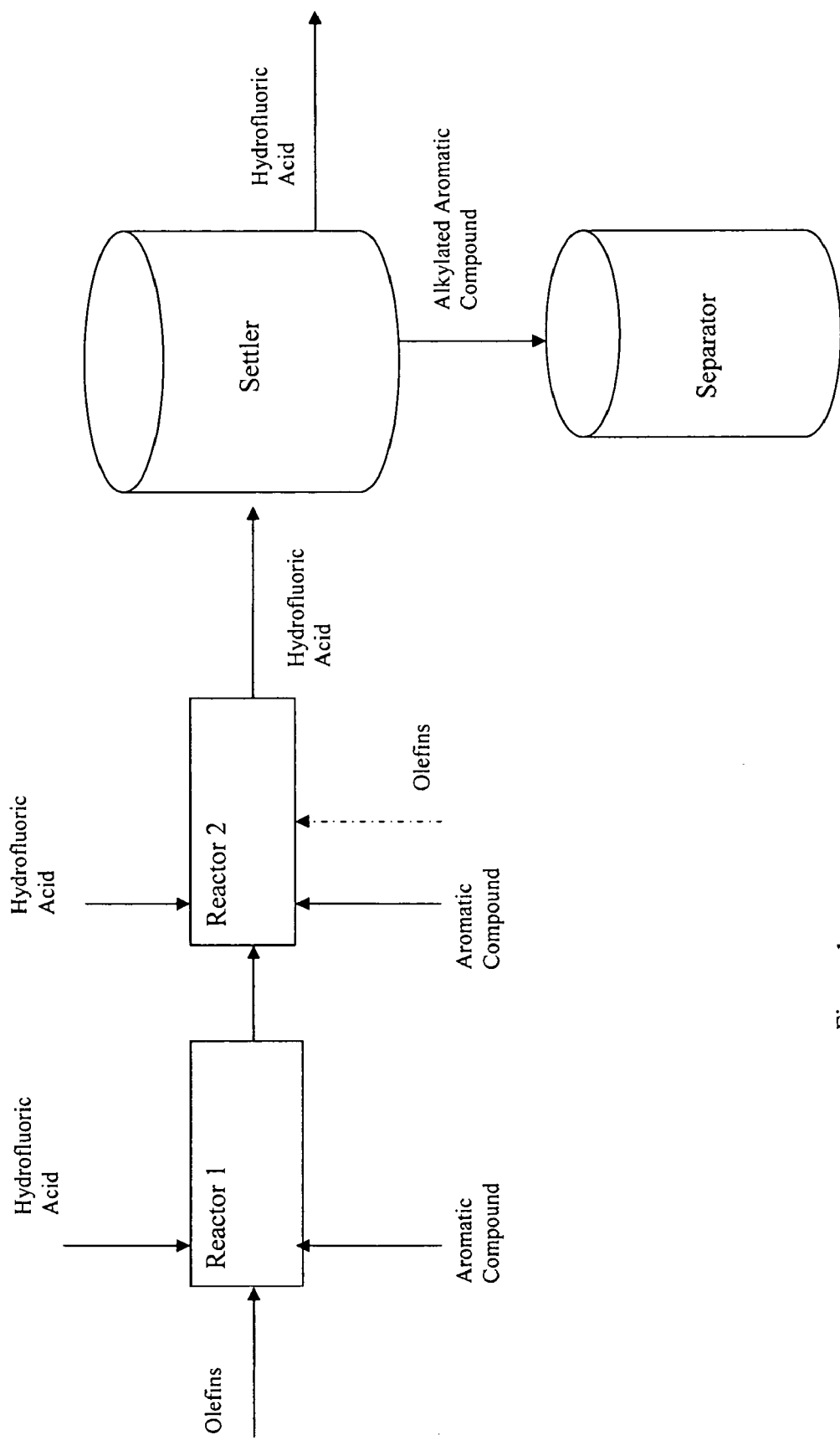
FIG. 1 discloses the alkylation process employed in the manufacture of the synthetic alkylaryl sulfonate of the present invention.

While the invention is susceptible to various modifications and alternative forms, specific embodiments thereof are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DEFINITIONS

Olefins—The term "olefins" refers to a class of unsaturated aliphatic hydrocarbons having one or more carbon-carbon double bonds, obtained by a number of processes. Those containing one double bond are called mono-alkenes, and those with two double bonds are called dienes, alkyldienes, or diolefins. Alpha olefins are particularly reactive because the double bond is between the first and second carbons. Examples are 1-octene and 1-octadecene, which are used as the starting point for medium-biodegradable surfactants. Linear and branched olefins are also included in the definition of olefins.

Linear Olefins—The term "linear olefins," which include normal alpha olefins and linear alpha olefins, refers to olefins which are straight chain, non-branched hydrocarbons with at least one carbon-carbon double bond present in the chain.

Double-Bond Isomerized Linear Olefins—The term "double-bond isomerized linear olefins" refers to a class of linear olefins comprising more than 5% of olefins in which the carbon-carbon double bond is not terminal (i.e., the double bond is not located between the first and second carbon atoms of the chain).

Partially Branched Linear Olefins—The term "partially branched linear olefins" refers to a class of linear olefins comprising less than one alkyl branch per straight chain containing the double bond, wherein the alkyl branch may be a methyl group or higher. Partially branched linear olefins may also contain double-bond isomerized olefin.

Branched Olefins—The term "branched olefins" refers to a class of olefins comprising one or more alkyl branches per linear straight chain containing the double bond, wherein the alkyl branch may be a methyl group or higher.

$C_{12}$-$C_{30}^+$ Normal Alpha Olefins—This term defines a fraction of normal alpha olefins wherein the carbon numbers below 12 have been removed by distillation or other fractionation methods.

In one preferred embodiment of the present invention is a process for preparing a synthetic alkylaryl sulfonate comprising (a) reacting a first amount of at least one aromatic compound with a fist amount of a mixture of olefins selected from olefins having from about 8 to about 100 carbon atoms, in the presence of a strong acid catalyst; (b) reacting the product of (a) with an additional amount of at least one aromatic compound and an additional amount of strong acid catalyst and, optionally, with an additional amount of a mixture of olefins selected from olefins having from about 8 to about 100 carbon atoms, wherein the resulting product comprises at least about 85 weight percent of a 1, 2, 4 tri-alkylsubstituted aromatic compound; (c) sulfonating the product of (b); and (d) neutralizing the product of (c) with a source of alkali or alkaline earth metal or ammonia.

Aromatic Compound

At least one aromatic compound or a mixture of aromatic compounds may be used for the alkylation reaction in the present invention. Preferably the at least one aromatic compound or the aromatic compound mixture comprises at least one of monocyclic aromatics, such as benzene, toluene, xylene, cumene or mixtures thereof. The at least one aromatic compound or aromatic compound mixture may also comprise bi-cyclic and poly-cyclic aromatic compounds, such as naphthalenes. More preferably, the at least one aromatic compound or aromatic compound mixture is xylene, including all isomers (i.e., meta-, ortho- and para-), a raffinate of xylene isomerization, and mixtures thereof. Most preferably, the at least one aromatic compound is ortho-xylene.

Sources of Aromatic Compound

The at least one aromatic compound or the mixture of aromatic compounds employed in the present invention is prepared by methods that are well known in the art.

Olefins

Sources of Olefins

The olefins employed in this invention may be linear, isomerized linear, branched or partially branched linear. The olefin may be a mixture of linear olefins, a mixture of isomerized linear olefins, a mixture of branched olefins, a mixture of partially branched linear or a mixture of any of the foregoing.

The olefins may be derived from a variety of sources. Such sources include the normal alpha olefins, linear alpha olefins, isomerized linear alpha olefins, dimerized and oligomerized olefins, and olefins derived from olefin metathesis. Another source from which the olefins may be derived is through cracking of petroleum or Fischer-Tropsch wax. The Fischer-Tropsch wax may be hydrotreated prior to cracking. Other commercial sources include olefins derived from paraffin dehydrogenation and oligomerization of ethylene and other olefins, methanol-to-olefin processes (methanol cracker) and the like.

The olefins may also be substituted with other functional groups, such as carboxylic acid groups, heteroatoms, and the like, provided that such groups do not react with the strong acid catalyst.

The mixture of olefins is selected from olefins with carbon numbers ranging from about 8 carbon atoms to about 100 carbon atoms. Preferably, the mixture of olefins is selected from olefins with carbon numbers ranging from about 10 to about 80 carbon atoms, more preferred from about 14 to about 60 carbon atoms.

In another embodiment, preferably, the mixture of olefins is selected from linear alpha olefins or isomerized olefins containing from about 8 to about 100 carbon atoms. More preferably, the mixture of olefins is selected from linear alpha olefins or isomerized olefins containing from about 10 to about 80 carbon atoms. Most preferably, the mixture of olefins is selected from linear alpha olefins or isomerized olefins containing from about 14 to about 60 carbon atoms.

Furthermore, in a preferred embodiment, the mixture of olefins contains a distribution of carbon atoms that comprises from about 40 to about 90 percent $C_{12}$ to $C_{20}$ and from about 4 percent to about 15 percent $C_{32}$ to $C_{58}$. More preferably, the distribution of carbon atoms comprises from about 50 to about 80 percent $C_{12}$ to $C_{20}$ and from about 4 percent to about 15 percent $C_{32}$ to $C_{58}$.

The mixture of branched olefins is preferably selected from polyolefins which may be derived from $C_3$ or higher monoolefins (i.e., propylene oligomers, butylenes oligomers, or co-oligomers etc.). Preferably, the mixture of branched olefins is either propylene oligomers or butylenes oligomers or mixtures thereof.

Normal Alpha Olefins

Preferably, the mixture of linear olefins that may be used for the alkylation reaction is a mixture of normal alpha olefins selected from olefins having from about 8 to about 100 carbon atoms per molecule. More preferably the normal alpha olefin mixture is selected from olefins having from about 10 to about 80 carbon atoms per molecule. Most preferably, the normal alpha olefin mixture is selected from olefins having from about 12 to about 60 carbon atoms per molecule. An especially preferred range is from about 14 to about 60.

In one embodiment of the present invention, the normal alpha olefins are isomerized using at least one of two types of acidic catalysts, solid or liquid. A solid catalyst preferably has at least one metal oxide and an average pore size of less than 5.5 angstroms. More preferably, the solid catalyst is a molecular sieve with a one-dimensional pore system, such as SM-3, MAPO-11, SAPO-11, SSZ-32, ZSM-23, MAPO-39, SAPO-39, ZSM-22 or SSZ-20. Other possible acidic solid catalysts useful for isomerization include ZSM-35, SUZ-4, NU-23, NU-87 and natural or synthetic ferrierites. These molecular sieves are well known in the art and are discussed in Rosemarie Szostak's Handbook of Molecular Sieves (New York, Van Nostrand Reinhold, 1992) which is herein incorporated by reference for all purposes. A liquid type of isomerization catalyst that can be used is iron pentacarbonyl (Fe $(CO)_5$).

The process for isomerization of normal alpha olefins may be carried out in batch or continuous mode. The process temperatures may range from about 50° C. to about 250° C. In the batch mode, a typical method used is a stirred autoclave or glass flask, which may be heated to the desired reaction temperature. A continuous process is most efficiently carried out in a fixed bed process. Space rates in a fixed bed process can range from 0.1 to 10 or more weight hourly space velocity.

In a fixed bed process, the isomerization catalyst is charged to the reactor and activated or dried at a temperature of at least 150° C. under vacuum or flowing inert, dry gas. After activation, the temperature of the isomerization catalyst is adjusted to the desired reaction temperature and a flow of the olefin is introduced into the reactor. The reactor effluent containing the partially-branched, isomerized olefins is collected. The resulting partially-branched, isomerized olefins contain a different olefin distribution (i.e., alpha olefin, beta olefin; internal olefin, tri-substituted olefin, and vinylidene olefin) and branching content that the unisomerized olefin and conditions are selected in order to obtain the desired olefin distribution and the degree of branching.

Acid Catalyst

Typically, the alkylated aromatic compound may be prepared using strong acid catalysts (Bronsted or Lewis acids). The term "strong acid" refers to an acid having a $pK_a$ of less than about 4. The term "strong acid" is also meant to include mineral acids stronger than hydrochloric acid and organic acids having a Hammett acidity value of at least minus 10 or lower, preferably at least minus 12 or lower, under the same conditions employed in context with the herein described invention. The Hammett acidity function is defined as:

$$H_o = pK_{BH+} - \log(BH^+/B)$$

where B is the base and $BH^+$ its protonated form, $pK_{BH+}$ is the dissociation constant of the conjugate acid and $BH^+/B$ is the ionization ratio; lower negative values of $H_o$ correspond to greater acid strength.

Preferably, the strong acid catalyst is selected from a group consisting of hydrochloric acid, hydrofluoric acid, hydrobromic acid, sulfuric acid, perchloric acid, trifluoromethane sulfonic acid, fluorosulfonic acid, and nitric acid. Most preferred, the strong acid catalyst is hydrofluoric acid.

The alkylation process may be carried out in a batch or continuous process. The strong acid catalyst may be recycled when used in a continuous process. The strong acid catalyst may be recycled or regenerated when used in a batch process or a continuous process.

The strong acid catalyst may be regenerated after it becomes deactivated (i.e., the catalyst has lost all or some portion of its catalytic activity). Methods that are well known in the art may be used to regenerate the deactivated hydrofluoric acid catalyst.

Process for Preparing Alkylated Aromatic Compound

In one embodiment of the present invention, the alkylation process is carried out by reacting a first amount of at least one aromatic compound or a mixture of aromatic compounds with a first amount of a mixture of olefin compounds in the presence of a strong acid catalyst, such as hydrofluoric acid, in a first reactor in which agitation is maintained, thereby producing a first reaction mixture. The resulting first reaction mixture is held in a first alkylation zone under alkylation conditions for a time sufficient to convert the olefin to aromatic alkylate (i.e., a first reaction product). After a desired time, the first reaction product is removed from the alkylation zone and fed to a second reactor wherein the first reaction product is reacted with an additional amount of at least one aromatic compound or a mixture of aromatic compounds and an additional amount of strong acid catalyst and, optionally, with an additional amount of a mixture of olefin compounds wherein agitation is maintained. A second reaction mixture results and is held in a second alkylation zone under alkylation conditions for a time sufficient to convert the olefin to aromatic alkylate (i.e., a second reaction product). The second reaction product is fed to a liquid-liquid separator to allow hydrocarbon (i.e., organic) products to separate from the strong acid catalyst. The strong acid catalyst may be recycled to the reactor(s) in a closed loop cycle. The hydrocarbon product is further treated to remove excess un-reacted aromatic compounds and, optionally, olefinic compounds from the desired alkylate product. The excess aromatic compounds may also be recycled to the reactor(s).

In another embodiment of the present invention, the reaction takes place in more than two reactors which are located in series. Instead of feeding the second reaction product to a liquid-liquid separator, the second reaction product is fed to a third reactor wherein the second reaction product is reacted with an additional amount of at least one aromatic compound or a mixture of aromatic compounds and an additional amount of strong acid catalyst and, optionally, with an additional amount of a mixture of olefin compounds wherein agitation is maintained. A third reaction mixture results and is held in a third alkylation zone under alkylation conditions for a time sufficient to convert the olefin to aromatic alkylate (i.e., a third reaction product). The reactions take place in as many reactors as necessary to obtain the desired alkylated aromatic reaction product.

The total charge mole ratio of hydrofluoric acid to the mixture of olefin compounds is about 1.0 to 1 for the combined reactors. Preferably, the charge mole ratio of hydrofluoric acid to the mixture of olefin compounds is no more than about 0.7 to 1 in the first reactor and no less than about 0.3 to 1 in the second reactor.

The total charge mole ratio of the aromatic compound to the mixture of olefin compounds is about 7.5 to 1 for the combined reactors. Preferably, the charge mole ratio of the aromatic compound to the mixture of olefin compounds is no less than about 1.4 to 1 in the first reactor and is no more than about 6.1 to 1 in the second reactor.

Many types of reactor configurations may be used for the reactor zone. These include, but are not limited to, batch and continuous stirred tank reactors, reactor riser configurations, ebulating bed reactors, and other reactor configurations that are well known in the art. Many such reactors are known to those skilled in the art and are suitable for the alkylation reaction. Agitation is critical for the alkylation reaction and can be provided by rotating impellers, with or without baffles, static mixers, kinetic mixing in risers, or any other agitation devices that are well known in the art.

The alkylation process may be carried out at temperatures from about 0° C. to about 100° C. The process is carried out under sufficient pressure that a substantial portion of the feed components remain in the liquid phase. Typically, a pressure of 0 to 150 psig is satisfactory to maintain feed and products in the liquid phase.

The residence time in the reactor is a time that is sufficient to convert a substantial portion of the olefin to alkylate product. The time required is from about 30 seconds to about 30 minutes. A more precise residence time may be determined by those skilled in the art using batch stirred tank reactors to measure the kinetics of the alkylation process.

The at least one aromatic compound or mixture of aromatic compounds and the mixture of olefins may be injected separately into the reaction zone or may be mixed prior to injection. Both single and multiple reaction zones may be used with the injection of the aromatic compounds and the mixture of olefins into one, several, or all reaction zones. The reaction zones need not be maintained at the same process conditions.

The hydrocarbon feed for the alkylation process may comprise a mixture of aromatic compounds and a mixture olefins in which the molar ratio of aromatic compounds to olefins is from about 0.5:1 to about 50:1 or more. In the case where the molar ratio of aromatic compounds to olefin is >1.0 to 1, there is an excess amount of aromatic compounds present. Preferably an excess of aromatic compounds is used to increase reaction rate and improve product selectivity. When excess aromatic compounds are used, the excess un-reacted aromatic in the reactor effluent can be separated, e.g. by distillation, and recycled to the reactor.

Tri-Alkylsubstituted Alkylated Aromatic Compound

An intermediate product of the presently claimed invention is a tri-alkylsubstituted alkylated aromatic compound. Preferably, the resulting intermediate product comprises at least about 80 weight percent of a 1, 2, 4 tri-alkylsubstituted aromatic compound. More preferred, the resulting product comprises at least about 85 weight percent, even more preferred at least about 90 weight percent of a 1, 2, 4 tri-alkylsubstituted aromatic compound.

Preparation of Alkylaryl Sulfonate

In one embodiment of the present invention, the product prepared by the process described herein (i.e., alkylated aromatic compound: 1,2,4 tri-alkylsubstituted alkylbenzene; 1,2,3 tri-alkylsubstituted alkylbenzene and mixtures thereof) is further reacted to form a sulfonate.

Sulfonation

Sulfonation of the alkylaryl compound may then be performed by any method known to one of ordinary skill in the art. The sulfonation reaction is typically carried out in a continuous falling film tubular reactor maintained at about 55° C. The alkylaryl compound is placed in the reactor along with the sulfur trioxide diluted with air, sulfuric acid, chlorosulfonic acid or sulfamic acid, thereby producing alkylaryl sulfonic acid. Preferably, the alkylaryl compound is sulfonated with sulfur trioxide diluted with air. The charge mole ratio of sulfur trioxide to alkylate is maintained at about 0.8 to 1.1:1.

Neutralization of Alkylaromatic Sulfonic Acid

Neutralization of the alkylaryl sulfonic acid may be carried out in a continuous or batch process by any method known to a person skilled in the art to produce alkylaryl sulfonates. Typically, an alkylaryl sulfonic acid is neutralized with a source of alkali or alkaline earth metal or ammonia. Preferably, the source is an alkali or alkaline earth metal; more preferably, the source is an alkaline earth metal hydroxide, such as but not limited to, calcium hydroxide or magnesium hydroxide.

Other embodiments will be obvious to those skilled in the art.

The following examples are presented to illustrate specific embodiments of this invention and are not to be construed in any way as limiting the scope of the invention.

EXAMPLES

Examples 1-3

Alkylation of Ortho-Xylene with $C_{14-30+}$ NAO using Two Alkylation Reactors in Series The alkylated ortho-xylenes of Examples 1-3 were prepared in a continuous alkylation pilot plant using hydrofluoric acid (HF) in which two alkylation reactors (1.15 liter volume each) were in series followed by a 25 liter settler to separate the organic phase from the HF phase. All equipment was maintained under a pressure of 5 bar and the reactors and settler were jacketed to allow temperature control. In addition, the alkylation reactors were configured such that the ortho-xylene, normal alpha olefins (NAO) and HF could be fed to each reactor at a specified rate.

TABLE 1

| Reaction Conditions | Example | | |
|---|---|---|---|
| | 1 | 2 | 3 |
| Reactor 1 | | | |
| HF/Olefin Vol. Ratio | 0.7 | 0.7 | 0.7 |
| Xylene/Olefin CMR | 1.4 | 1.4 | 1.4 |
| Temperature (° C.) | 64 | 70 | 70 |
| Reactor 2 | | | |
| HF/Olefin Vol. Ratio | 1 | 1 | 1 |
| Xylene/Olefin CMR | 7.5 | 7.5 | 7.5 |
| Temperature (° C.) | 60 | 60 | 60 |

* The CMR in Reactor is the cumulative ratio, which includes Reactor 1 reactants.

Following the settler, the organic phase was removed through a valve and allowed to expand to atmospheric pressure. The HF acid phase was separated. The resulting organic phase was then distilled under vacuum to remove the excess ortho-xylene. Results are shown in Table 1.

The alkylation feedstock consisted of a mixture of o-xylene and $C_{14}$-$C_{30}^+$ normal alpha olefins with a molar ratio of xylene/olefin=7.5. The olefin used to make this feed was a blend of commercial $C_{14}$-$C_{30+}$ cuts. The distribution of olefins in the feed is shown in Table 2.

TABLE 2

| Olefin Feedstock Distribution | |
|---|---|
| Carbon Number | Wt-% |
| 14 | 24.4 |
| 16 | 18.4 |
| 18 | 15.2 |
| 20 | 9.7 |

TABLE 2-continued

Olefin Feedstock Distribution

| Carbon Number | Wt-% |
|---|---|
| 22 | 8.2 |
| 24 | 5.7 |
| 26 | 5.4 |
| 28 | 5.0 |
| 30+ | 8.0 |

The feed mixture was stored under dry nitrogen during use. Because of the waxy nature of the alpha olefin, the alkylation feed mixture was heated to 50° C. to keep all the olefin in solution. O-Xylene was also stored under dry nitrogen during use.

Examples 4-7

General Procedure for Sulfonation and Neutralization of Alkyl Ortho-Xylene Alkylate Sulfonation of the alkylxylene was performed in a continuous falling film flow reactor by contacting the alkylxylene with a stream of air and sulfur trioxide. The molar ratio of the alkylxylene to sulfur trioxide ranged from was about 1. Detailed values are given in Table 3. The reactor jacket was maintained around 60° C. The sulfonic acid product was titrated potentiometrically with a standardized cyclohexylamine solution to determine the weight percent of the sulfonic acid (as $HSO_3$) and the sulfuric acid ($H_2SO_4$) in the samples. Results are shown in Table 3.

The resulting alkyl ortho-xylene sulfonic acids were converted to their corresponding sodium salt by treatment with one equivalent of aqueous NaOH (50% aqueous NaOH solution). The salts were evaluated by the Fresh Interfacial Tension (FIT) Method. This procedure was as follows:

1) A 3.0 wt % stock solution of alkyl ortho-xylene sodium sulfonate was prepared in distilled water;
2) A stock solution of 3.0 wt % co-solvent (diethylene glycol n-butyl ether) and stock 3.0 wt-% sodium chloride solution in distilled water were prepared;
3) The alkyl ortho-xylene sodium stock sulfonate solution and stock solution of co-solvent/sodium chloride were blended to achieve the appropriate salinity (0.1, 0.2, 0.3, 0.4, 0.5 wt % sodium chloride) and constant concentration of the sodium sulfonate and co-solvent.

All samples contained 0.2 wt % alkyl ortho-xylene sodium sulfonate and 0.067 wt % co-solvent (weight ration 3/1 of sodium sulfonate: co-solvent).

To measure the interfacial tension, the sodium sulfonate/co-solvent solutions were each placed in the capillary of a Temco Model 501 Tensiometer followed by approximately 2 µl of Minas crude oil (pre-heated so to be well above its Wax Appearance Temperature (WAT)). The samples were heated to 200° F., spun in the Tensiometer at two or three rotation speeds (300, 500 and sometimes 8000 rpm), and their drop geometries measured over 1-3 hours. The FIT measure at the different speeds and generally good agreement was observed between the different measurements. Rotation speed was adjusted in some cases to achieve an oil drop geometry with an aspect ratio of length /width of 4 or greater and allowed to expand to atmospheric pressure.

Table 4 summarizes the FIT measurements of the alkyl ortho-xylene sodium sulfonates. Without surfactant, FIT measurements for Minas crude are on the order of 10-20 dynes/cm. FIT measurements for the alkyl ortho-xylene sodium sulfonates of this invention are all less than 0.01 dynes/cm. Such surfactants are considered to be useful in recovering oil in low salinity reservoirs. Optimal salinity is the salinity where the interfacial tension is lowest, which in Examples 4-7 is 0.2% NaCl.

TABLE 3

Properties of ortho-Xylene Alkylates Prepared by Hydrofluoric Acid Catalyzed Alkylation

| Example | Relative % Aromatic Ring Attachment % 1, 2, 3 | Relative % Aromatic Ring Attachment % 1, 2, 4- | % Alkyl Chain Attachment* | | | |
|---|---|---|---|---|---|---|
| | | | 2-Aryl-Alkane | 3-Aryl-Alkane | 4-Aryl-Alkane | 4+Aryl-Alkane |
| 1 | 11.0 | 89.0 | 11 | 10 | 15.6 | 63.4 |
| 2 | 13.0 | 87.0 | 12.4 | 10.7 | 16.0 | 60.9 |
| 3 | 10.0 | 90.0 | 11.2 | 11.1 | 15.5 | 62.2 |

*% Alkyl Chain Attachment refers to the carbon number along the alkyl chain to which the aromatic ring is attached.

TABLE 4

Properties of the Alkyl ortho-Xylene Sulfonic Acids and the FIT Results of the Alkyl ortho-Xylene Sodium Sulfonates (Corresponding to Table 3)

| Example | Alkylate Example No. | CMR $SO_3$/Alkylate | Sulfonic Acids % $RSO_{3\,as}$ HSO3 | % $H_2SO_4$ | FIT Dynes/cm | Optimal Salinity, % NaCl |
|---|---|---|---|---|---|---|
| 4 | 1 | 0.98 | 15.2 | 0.67 | 0.0070 | 0.2 |
| 5 | 1 | 1.02 | 17.1 | 0.56 | 0.0009 | 0.2 |
| 6 | 3 | 0.98 | 15.6 | 1.20 | 0.0010 | 0.2 |
| 7 | 2 | 1.05 | 16.2 | 0.97 | 0.0030 | 0.2 |

Example 8

Infrared Method to Determine Relative Percentage of 1, 2, 3 Alkyl and 1, 2, 4-Alkyl Aromatic Ring Attachment The infrared spectrum of a sample of alkylated ortho-xylene product was obtained using an infrared spectrometer (Thermo model 4700) equipped with a rebounce diamond attenuated reflectance cell. The absorbance spectrum of the sample between 600 and 1000 $cm^{-1}$ was displayed and the peaks at about 780, 820, and 880 $cm^{-1}$ were integrated. The relative percentage area of each peak was calculated and the percent 1, 2, 3-alkyl aromatic content is represented by the relative area percentage of the 780 $cm^{-1}$ peak.

Example 9

Carbon Nuclear Magnetic Resonance Method to Determine the Percent Alkyl Attachment Position to the Aromatic Ring Quantitative $^{13}C$ NMR spectra were obtained on a 300 MHz Varian Gemini NMR (75 MHz carbon) using about 1.0 g of sample dissolved in about 3.0 mL of 0.5 M chromium $(acac)_3$ in chloroform-d contained in a 10 mm NMR tube. The transmitter pulse sequence (delay (2.2 s), 90 pulse acquisition (0.853 s) was employed with the decoupler (WALTZ-16)

gated off during the delay and on during acquisition. Cursory examination of the T1's for the quaternary carbons at our $CR(acac)_3$ levels indicated they were about 0.4-0.5 s. Thus, the relaxation delay was always more than four times the longest T1. We believe this is sufficient to allow residual NOE to die away between pulse excitations even though the decoupler duty cycle is above the recommended 5-10% range for quantitative experiments. Integration of the $^{13}C$ NMR spectrum was carried out with no base-line correction.

The integrated peak intensity for the quartemary carbons (Q) on the aromatic ring carbons substituted with the long chaing alkyl group and the methane (benzylic) carbons (M) of the long chain alkyl groups where the long chain alkyl group is attached to the aromatic ring are used to calculate the percent alkyl attachment position. For the different alkyl chain attachments, the following assignments were made (in ppm downfield from TMS): 2-position (R=Methyl); Q=145.475 ppm, M=39.56 ppm; 3-position (R=Ethyl), Q=143.502 ppm, M=47.50 ppm; 4-position (R=n-Propyl), Q=143.86 ppm, M=45.4 ppm; 5-position and higher (R=greater than n-Propyl), Q=143.86, M=45.69 ppm. The NMR spectrum is integrated and the signals between 143 to 147 ppm, and 39 to 48 ppm are enlarged and integrated. For the 143 to 147 ppm region integral, the relative amount of R=Methyl, R=Ethyl and R=n-Propyl were determined. For the 39-48 ppm region integral, one obtains the relative amounts of R=Methyl, R=Ethyl, R=n-Propyl and R>n-Propyl. To perform the calculations, first, check to see that the integrals for each aromatic carbon is the same. Sum the integrals for each of the Q and M peaks and calculate the percentage attachment from both the aromatic quarternary (Q) and aliphatic methine (M) integrals of the assigned peaks. For example, the amount of 2-attachment from the integration of the aromatic quaternary carbons would equal the integral for the 145.475 ppm signal divided by the total of the integrals for the 145.475 ppm peak plus the integral for the 143.502 ppm peak plus the integral for the 143.86 ppm peak. The aliphatic methine carbons provide the 2-, 3-, 4-, and >4-alkyl attachment while the aromatic quaternary carbons provide only the 2-, 3-, and 4-alkyl attachment values. The attachment values determined by the aliphatic methine and the aromatic quaternary carbons agree reasonably well.

What is claimed is:

1. A process for preparing a synthetic alkylaryl sulfonate comprising
   (a) reacting a first amount of at least one aromatic compound with an amount of a mixture of olefins selected from olefins having from about 8 to about 100 carbon atoms, in the presence of a strong acid catalyst;
   (b) reacting the product of (a) with an additional amount of at least one aromatic compound and an additional amount of strong acid catalyst and, optionally, with an additional amount of a mixture of olefins selected from olefins having from about 8 to about 100 carbon atoms, wherein the resulting product comprises at least about 80 weight percent of a 1,2,4tri-alkylsubstituted aromatic compound;
   (c) sulfonating the product of (b); and
   (d) neutralizing the product of (c) with a source of alkali or alkaline earth metal or ammonia.

2. The process according to claim 1 wherein the product of (b) further comprises 1,2,3tri-alkylsubstituted aromatic compound or mixtures thereof.

3. The process according to claim 1 wherein the source of alkali or alkaline earth metal is hydroxide.

4. The process according to claim 1 wherein sulfonating the product occurs when the product of (b) is reacted with sulfur trioxide which has been diluted with air.

5. The process according to claim 1 wherein the at least one aromatic compound is selected from unsubstituted aromatic compounds, monosubstituted aromatic compounds, and disubstituted aromatic compounds.

6. The process according to claim 5 wherein the at least one aromatic compound is selected from benzene, toluene, meta-xylene, para-xylene, ortho-xylene, and mixtures thereof.

7. The process according to claim 6 wherein the at least one aromatic compound is selected from meta-xylene, para-xylene, ortho-xylene and mixtures thereof.

8. The process according to claim 7 wherein the at least one aromatic compound is ortho-xylene.

9. The process according to claim 1 wherein the mixture of olefins in step (a) or step (b) is a mixture of linear olefins, a mixture of linear isomerized olefins, a mixture of branched olefins, a mixture of partially branched olefins, or a mixture thereof.

10. The process according to claim 9 wherein the mixture of olefins in step (a) or step (b) is a mixture of linear olefins.

11. The process according to claim 10 wherein the mixture of linear olefins is a mixture of normal alpha olefins.

12. The process according to claim 11 wherein the mixture of linear olefins comprises olefins derived through cracking of petroleum wax or Fischer Tropsch wax.

13. The process according to claim 12 wherein the Fischer Tropsch wax is hydrotreated before cracking.

14. The process according to claim 9 wherein the mixture of olefins comprises from about 8 carbon atoms to about 100 carbon atoms.

15. The process according to claim 14 wherein the mixture of olefins is derived from linear alpha olefins or isomerized olefins containing from about 8 to 100 carbon atoms.

16. The process according to claim 15 wherein the mixture of olefins is derived from linear alpha olefins or isomerized olefins containing from about 10 to about 80 carbon atoms.

17. The process according to claim 16 wherein the mixture of olefins is derived from linear alpha olefins or an isomerized olefins containing from about 14 to about 60 carbon atoms.

18. The process according to claim 10 wherein the mixture of linear olefins is a mixture of linear internal olefins which have been derived from olefin metathesis.

19. The process according to claim 1 wherein the mixture of olefins is a mixture of branched olefins.

20. The process according to claim 19 wherein the mixture of branched olefins comprises polyolefin compounds derived from $C_3$ or higher monoolefins.

21. The process according to claim 20 wherein the polyolefin compound is either polypropylene or polybutylene.

22. The process according to claim 21 wherein the polyolefin compound is polypropylene.

23. The process according to claim 22 wherein the polyolefin compound is polybutylene.

24. The process according to claim 1 wherein the strong acid catalyst is selected from the group consisting of hydrochloric acid, hydrofluoric acid, hydrobromic acid, sulfuric acid, perchloric acid, trifluoromethanesulfonic acid, fluorosulfonic acid, and nitric acid.

25. The process according to claim 24 wherein the strong acid catalyst is hydrofluoric acid.

26. The process according to claim 1 wherein strong acid catalyst may be recycled.

27. The process according to claim 1 wherein the reaction takes place in a continuous process.

28. The process according to claim 1 wherein, in step (b), the product of step (a) is reacted with an additional amount of at least one aromatic compound and an additional amount of a mixture of olefins selected from olefins having from about 8 to about 100 carbon atoms.

29. The process according to claim 1 wherein the resulting product comprises at least about 85 weight percent of a 1,2,4,tri-alkylsubstituted aromatic compound.

* * * * *